United States Patent [19]

Schena et al.

[11] Patent Number: 5,166,351

[45] Date of Patent: Nov. 24, 1992

[54] MONO-N,N-DIMETHYL-4-AMINOPYRIDINIUM SN-GLYCEROL-3-PHOSPHATE DERIVATIVES

[75] Inventors: David Schena, Brighton; Jeffrey Davis, Watertown, both of Mass.

[73] Assignee: Genzyme Corporation, Cambridge, Mass.

[21] Appl. No.: 577,351

[22] Filed: Aug. 31, 1990

Related U.S. Application Data

[62] Division of Ser. No. 395,678, Aug. 18, 1989, abandoned.

[51] Int. Cl.$^5$ ............................................. C07D 213/74
[52] U.S. Cl. .................................. 546/304; 540/597; 546/193; 546/275; 546/281
[58] Field of Search ............... 546/193, 275, 281, 304; 540/597

[56] References Cited

PUBLICATIONS

Gupta et al, *Proceedings of the National Academy of Sciences USA*, 74 No. 10, Oct. 1977, 4315–4319.
Lapidot et al, *Journal of the American Chemical Society*, vol. 87, No. 23, Dec. 1965, 5522–5523.

*Primary Examiner*—Joseph Paul Brust
*Assistant Examiner*—Jacqueline Haley

[57] ABSTRACT

Provided is a novel salt of sn-glycerol-3-phosphate comprising mono-N,N-dimethyl-4-aminopyridine along with methods for making same and using same for the production of diacyl phosphatidic acids.

4 Claims, 1 Drawing Sheet

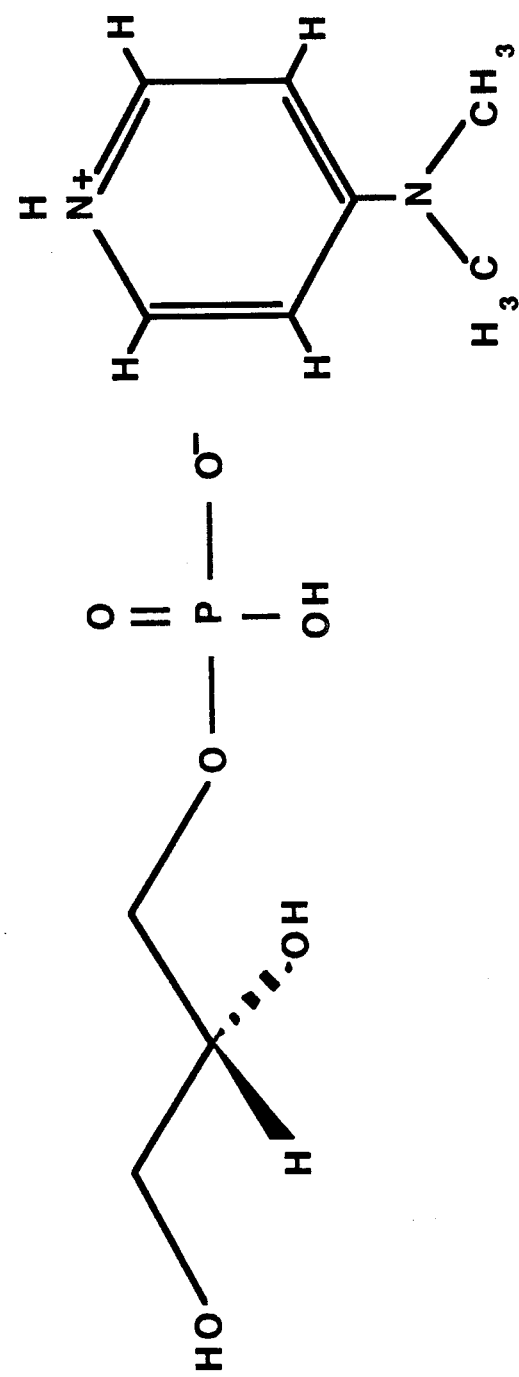
Figure

5,166,351

MONO-N,N-DIMETHYL-4-AMINOPYRIDINIUM SN-GLYCEROL-3-PHOSPHATE DERIVATIVES

This is a divisional of co-pending application Ser. No. 395,678 filed on Aug. 18, 1989 and now abandoned.

BACKGROUND OF THE INVENTION

The present invention pertains to the production of a crystalline salt of sn-glycerol-3-phosphate and to its subsequent use in the direct preparation of diacyl phosphatidic acids. More specifically, this invention relates to the production of the mono-N,N-dimethyl-4-aminopyridinium salt of sn-glycerol-3-phosphate (G-3-P(DMAP)$_1$), a uniquely crystalline and anhydrous form of the phosphate. In addition, this invention relates to the method of direct acylation of the aforementioned N,N-dimethyl-4-aminopyridinium sn-glycerol-3-phosphate salt with fatty acid anhydrides so as to provide new methods for production of diacyl phosphatidic acids.

Diacyl phosphatidic acids are useful precursors for the synthesis of phospholipids which are major components of cellular membranes. Diacyl phosphatidic acids may be prepared by the acylation of various salt forms of sn-glycerol-3-phosphate. For example, Y. Lapidot and Z. Selinger in J. Am. Chem. Soc., Vol 87, 5522–5523 (1965) described the synthesis of diacyl phosphatidic acids via the acylation of pyridinium sn-glycerol-3-phosphate. The Lapidot et al. method gave acceptable yields (70%-80%) of the desired diacyl phosphatidic acids without significant formation of by-products, but on a small scale (0.4 mmol). Gupta et al. in Proc. Nat. Acad. Sci., Vol. 74, 4315–4319 (1977) described an improvement on the method of Lapidot et al., wherein the basic catalyst, N,N-dimethyl-4-aminopyridine, was added to enhance the reactivity of the fatty acid anhydride towards nucleophilic attack by pyridinium sn-glycerol-3-phosphate. According to Gupta et al., pyridinium sn-glycerol-3-phosphate gave superior yields (87%) of diacyl phosphatidic acid when reacted with fatty acid anhydride (3 equiv) and N,N-dimethyl-4-aminopyridine (4 equiv). While the method of Gupta et al. is amenable for production of diacyl phosphatidic acids on a millimolar scale, there are serious limitations in the large-scale synthesis of diacyl phosphatidic acids using this method.

It is one aspect of the present invention to provide new methods for the synthesis of diacyl phosphatidic acids which are useful for large-scale application.

Another limitation to these conventional methods for diacyl phosphatidic acid production is the required use of pyridinium sn-glycerol-3-phosphate. As described by Gupta et al., pyridinium sn-glycerol-3-phosphate salt is a hygroscopic and gummy oil which consequently poses several disadvantages in large-scale acylation reactions. As an intractable and hygroscopic oil, the pyridinium sn-glycerol-3-phosphate is difficult to accurately weigh thereby making quantification of reaction stoichiometry problematic. The difficulty in completely removing water and alcohols from the pyridinium sn-glycerol-3-phosphate poses another significant disadvantage.

Because the reaction conditions for diacyl phosphatidic acid production must be free of water and alcohol, large-scale diacyl phosphatidic acid synthesis using pyridinium sn-glycerol-3-phosphate poses substantial disadvantages in order to render the salt anhydrous and solvent-free. Both the Lapidot et al. and the Gupta et al. methods are labor intensive and require repeated addition of dry pyridine and subsequent evaporation of the solvent to render the pyridinium sn-glycerol-3-phosphate salt anhydrous.

It is another aspect of the present invention to avoid the use of pyridinium sn-glycerol-3-phosphate in the synthesis of diacyl phosphatidic acid.

Another serious drawback to the methods of Lapidot et al. and Gupta et al. is the indirect formulation of the pyridinium sn-glycerol-3-phosphate itself. Conventional methods known to date provide for the derivation of pyridinium sn-glycerol-3-phosphate from other sn-glycerol-3-phosphate salt forms. The other known crystalline salts of sn-glycerol-3-phosphate are the barium, calcium, sodium, monocyclohexylammonium and the dicyclohexylammonium sn-glycerol-3-phosphates. Both the barium and dicyclohexylammonium salts are generally prepared solely as a means to isolate the sn-glycerol-3-phosphate (C. F. Crans et al. in J. Am. Chem. Soc., Vol 107, 7019 (1986)). However, neither salt may be used directly for diacyl phosphatidic acid production since the barium salt is insoluble in the requisite organic reaction medium and the dicyclohexylammonium salt is not compatible with the coreactant fatty-acid anhydrides. To make either the barium or cyclohexylammonium salts compatible it is necessary to convert them to the pyridinium salt of sn-glycerol-3-phosphate if an acylation reaction is to be conducted. Such a conversion is a laborious process requiring exchange of the counter-ion for pyridine via the use of an ion-exchange resin. The solvent used to convert the salt to the pyridinium sn-glycerol-3-phosphate must be aqueous pyridine. The subsequent isolation of the pyridinium sn-glycerol-3-phosphate from the aqueous solution and the drying of the salt is, however, too expensive in terms of time and effort to make this procedure practical on a kilogram scale.

It is yet another aspect of the present invention to avoid the use of barium and dicyclohexylammonium salts in the preparation of diacyl phosphatidic acids.

It is still yet another aspect of the present invention to provide a method to readily isolate a salt of sn-glycerol-3-phosphate in a crystalline and anhydrous form which can be subsequently directly acylated to economically form phosphatidic acids, and to provide a process for the synthesis of diacyl phosphatidic acids and other phospholipids from sn-glycerol-3-phosphate.

SUMMARY OF INVENTION

In accordance with the various principles and aspects of the present invention, there is described a convenient and practical large scale production of N,N-dimethyl-4-aminopyridinium sn-glycerol-3-phosphate and the direct use of this salt for the production of diacyl phosphatidic acids. In general the invention features, in one aspect, the production of a crystalline and anhydrous salt of sn-glycerol-3-phosphate. In another aspect the invention features the use of the crystalline and anhydrous salt, N,N-dimethyl-4-aminopyridinium sn-glycerol-3-phosphate, shown in the FIGURE, in the direct formation of diacyl phosphatidic acids, themselves useful as intermediates in the synthesis of other phospholipids, most especially diacyl phosphatidyl esters. The preparation of such phospholipids using the foregoing is also contemplated by the present invention.

The N,N-dimethyl-4-aminopyridinium sn-glycerol-3-phosphate salt of the present invention, when compared to the conventional pyridinium sn-glycerol-3-phosphate salt, exhibits enhanced solubility and reactivity in organic solvents such as methylene chloride and chloroform. The enhanced solubility and reactivity greatly facilitates and now makes practical for the first time, the large scale production of diacyl phosphatidic acids and their derivatives.

BRIEF DESCRIPTION OF THE DRAWING

Furthur understanding of the present invention may be had by reference to the accompanying FIGURE showing a structural presentation of the novel composition of the present invention, N,N-dimethyl-4-aminopyridinium sn-glycerol-3-phosphate.

DETAILED DESCRIPTION OF THE INVENTION AND BEST MODE

The crystalline and anhydrous N,N-dimethyl-4-aminopyridinium sn-glycerol-3-phosphate is ideally obtained as follows. The free acid form of sn-glycerol-3-phosphate is preferably mixed with an equimolar amount of the base N,N-dimethyl-4-aminopyridine in an alcoholic solvent until both reactants are in solution. The most preferred solvent is methanol. Other possible solvents which may be used include ethanol or n-propanol. One may also substitute for sn-glycerol-3-phosphate analogues thereof wherein, for example, the $C_1$ hydroxyl may be replaced by —Cl, —Br, —SH, —OCH$_3$, —CH$_2$OH or —CH$_2$CH$_3$.

The preferred method of isolating the crude N,N-dimethyl-4-aminopyridinium sn-glycerol-3-phosphate comprises removal of the methanol via in vacuo concentration. The resulting oil contains residual methanol and N,N-dimethyl-4-aminopyridinium hydrochloride as the major contaminants.

The preferred method for removing the major contaminants comprises dissolution of the oil in isopropyl alcohol and, following addition of an organic solvent, precipitation of the N,N-dimethyl-4-aminopyridinium sn-glycerol-3-phosphate as an off-white crystalline solid. The preferred organic solvent used for effecting the precipitation of the N,N-dimethyl-4-aminopyridinium sn-glycerol-3-phosphate is acetone. The preferred ratio of acetone to isopropyl alcohol, while not crucial, should be 10 volumes to 1 volume respectively. The range of acetone to isopropyl alcohol volumes can vary from approxiametely 5-to-1 to about 100-to-1 respectively.

The resulting suspension of precipitated salt is then vigorously stirred so as to ensure no formation of oily residue. Isolation of the sn-glycerol-3-phosphate salt is ideally effected by filtration.

To ensure complete removal of volatile solvent contaminants it is preferred that the crystalline salt be dried in vacuo prior to both analyses. The analysis of the resulting N,N-dimethyl-4-aminopyridinium sn-glycerol-3-phosphate is best done by using either one or most preferably both of the two following procedures.

The first preferred analytical procedure is an enzymatic assay for sn-glycerol-3-phosphate. The enzymatic assay, according to Bergmeyer et al. in Biochem. Z, Vol 33, 471 (1961), depends on the quantitative conversion of sn-glycerol-3-phosphate to 1-phospho-3-hydroxyacetone by an NADH-requiring dehydrogenase, preferably sn-glycerol-3-phosphate dehydrogenase. A second preferred analytical procedure for the N,N-dimethyl-4-aminopyridinium sn-glycerol-3-phosphate is the high-resolution proton magnetic resonance spectrum of the salt. This analytical test allows for the accurate quantification of the equivalents of dimethylaminopyridine per equivalent of sn-glycerol-3-phosphate in the salt. The preferred ratio of N,N-dimethyl-4-aminopyridine to sn-glycerol-3-phosphate is 1:1. It is preferred that the purity of the N,N-dimethyl-4-aminopyridinium sn-glycerol-3-phosphate salt as determined by both analyses be greater than 98%.

If the aforementioned analyses indicate that the salt does not meet the preferred purity criteria, a second purification step should be performed. The preferred method is to resuspend the crystalline salt in isopropyl alcohol and stir the suspension vigorously overnight. The volume of isopropyl alcohol is not critical but the preferred volume will be about 20 ml per gram of salt. Filtration of the suspension after prolonged stirring gives material of greater than 98% purity when reassayed using the two aforementioned analytical procedures. The major contaminant, N,N-dimethyl-4-aminopyridinium hydrochloride, is completely soluble in the isopropyl alcohol while the sn-glycerol-3-phosphate salt is only minimally soluble.

Acylation of the crystalline and anhydrous N,N-dimethyl-4-aminopyridinium sn-glycerol-3-phosphate is effected as follows:

The N,N-dimethyl-4-aminopyridinium sn-glycerol-3-phosphate salt is dissolved in an organic solvent and the base N,N-dimethyl-4-aminopyridine and a fatty-acid anhydride are added to the solution. The organic solvent used may be either dichloromethane, chloroform, or carbon tetrachloride with chloroform being most preferred. The ratio of sn-glycerol-3-phosphate salt to base and the ratio of sn-glycerol-3-phosphate salt to fatty-acid anhydride is not crucial but the preferred ratios are 1 molar equivalent of sn-glycerol-3-phosphate salt to 9 molar equivalents of N,N-dimethyl-4-aminopyridine, and 1 molar equivalent of sn-glycerol-3-phosphate salt to 5 equivalents of fatty-acid anhydride.

While the reaction time is also not crucial, it has been found preferable to employ a reaction time of approximately 72 hours. The reaction temperature may vary from room temperature (25° C.) to solvent reflux temperatures and is not crucial. For reactions containing myristic anhydride (C=14) and palmitic anhydride (C=16), the preferred reaction temperature is 25° C., while for longer-chain fatty-acid anhydrides, which tend to be less soluble, such as stearic anhydride (C=18), the preferred reaction temperature is on the order of 60° C. so as to aid in dissolution of the fatty-acid anhydride.

The reaction may be conveniently terminated by quenching with a methanol: $H_2O$ mixture. The ratio of methanol to water can be varied from 1 to 10 parts methanol to 1 part water. It is most preferred to use a ratio of 1 part methanol to 4 parts water, although this ratio is not critical, for quenching the acylation reaction. The resultant diacyl phosphatidic acid products may be purified from the reaction mixture by a preferred sequence of 1) an acid wash to remove residual dimethylaminopyridine and 2) chromatography to remove the fatty acid hydrolysis by-products. It is preferred to wash an organic solution of the hydrolyzed reaction mixture with an acidic aqueous solution, most preferably 1N HCl, so as to remove the excess base. Subsequently, the organic layer, containing product phosphatidic acid and residual fatty acids, may then be advantageously fractionated by a variety of chromatographic techniques such as those employing silica gel (Gupta et al.).

Once isolated, the diacyl phosphatidic acid may be further purified by recrystallization from organic solvents, with the preferred solvents being methanol and ethanol.

Further understanding of the invention will be had by a detailed study of the following examples. These examples are given by way of illustration and are not intended to limit the invention.

EXAMPLE 1

Preparation of N,N-Dimethyl-4-aminopyridinium sn-Glycerol-3-Phosphate (G-3-P (DMAP)$_1$)

To 100 g of sn-glycerol-3-phosphate, enzymatically prepared from sn-glycerol and ATP according to Whitesides et. al. in J. Am. Chem. Soc., Vol 107, 7019–7023 (1985), and dissolved in 500 ml of methanol, was added 66 g of N,N-dimethyl-4-aminopyridine (DMAP) obtained from Reilly Tar Co. The methanolic reaction mixture was vigorously stirred at room temperature until all the DMAP was in solution.

The methanol was removed in vacuo to yield a heavy oil. The oil was dissolved in 150 ml of isopropyl alcohol and 1.5 liters of acetone was added to the solution. An oily precipitate was formed upon addition of the acetone. The precipitate was dispersed in solution by vigorous stirring for 18 hours. Filtration of the precipitate and in vacuo drying yielded a fine crystalline, off-white solid (44 g, 60% molar yield).

The crystalline G-3-P (DMAP)$_1$ so produced was analyzed by enzymatic assay and found to be 88% G-3-P by weight. A $^1$H-NMR spectrum indicated the contaminating material to be DMAP-HCl salt. The impure material was resuspended in 500 ml of isopropyl alcohol and stirred overnight at room temperature. The suspended material was collected by conventional paper filtration and dried in vacuo to yield G-3-P (DMAP)$_1$ (m.p. 128°–130° C.) which was of 100% purity as judged by enzyme assay. A $^1$H-NMR confirmed the structure of the salt: (D$_2$O)ppm 7.9 (d)2H 6.8(d)2H, 3.82(m) and 3.64(m)5H, 3.1(s)6H.

EXAMPLE 2

Preparation of Dipalmitoyl Phosphatidic Acid (DPPA) by Acylation of N,N-Dimethyl-4-Aminopyridinium sn-Glycerol-3-Phosphate (G-3-P (DMAP)$_1$)

In this example the acylation of G-3-P (DMAP)$_1$ was carried out at elevated temperatures (60° C.). G-3-P (DMAP)$_1$ (5 g, 15.2 mmol) from Example 1, palmitic anhydride (37.5 g, 75.9 mmol) (Aldrich) and DMAP (16.7, 137 mmol) (Reilly Tar Co.) were suspended in 150 ml of dry chloroform. The reaction mixture was heated at reflux with vigorous stirring for 2 hours. At this time all reactants were in solution. The reaction mixture was then stirred at room temperature for 18 hours. The reaction mixture was then hydrolyzed by adding an equal volume of MeOH:H$_2$O (4:1). The resultant aqueous phase was acidified to pH 1 with the addition of concentrated HCl.

The organic layer was separated and washed three times with equal volumes of MeOH:H$_2$O:CHCl$_3$ (48:47:3). The organic layer was collected and reduced in vacuo to one half its original volume. This volume contains the desired dipalmitoyl phosphatidic acid and the fatty acid hydrolysis byproducts. Such byproducts may be advantageously removed using silica gel chromatography techniques as described by Gupta et al. The fractions containing the dipalmitoyl phosphatidic acid are then ideally combined and then concentrated in vacuo to remove the chromatography solvent. The resulting solid may then be further purified by acetone precipitation or methanol recrystallization. Characterization of the resultant product can be expected to yield a chemical purity of about 99 % with a melting point of 155°–156° C. Dipalmitoyl phosphatidic acid thusly prepared will ideally be characterized by the following: R$_f$=0.39, silica gel 60F$_{254}$ (Merck), CHCl$_3$—MeOH—H$_2$O (65:25:4); 400 MHZ $^1$H NMR (D$_2$O) ppm 5.2 (d) 1H, 4.38 (d) 1H, 4.16 (dd) 1H, 3.92 (m) 2H, 2.29 (dd) 4H, 1.20 (m) 56H, 0.87 (t) 6H.

Following a detailed study of the foregoing, those skilled in the art will readily recognize that numerous changes may be made with respect to reaction conditions (e.g. buffers, temperatures, reaction times) without departing from the substance, spirit or scope of the present invention.

What is claimed is:

1. The crystalline N,N-dialkyl-4-aminopyridinium salt represented by the following formula:

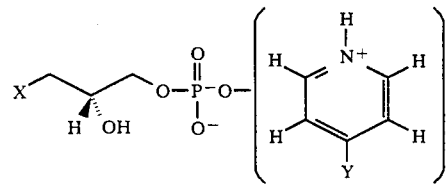

wherein X is selected from the group consisting of —OH, —Cl —Br, —SH, —OCH$_3$, —CH$_2$OH and —CH$_2$CH$_3$ and: wherein Y is (i)

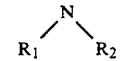

wherein R$_1$ and R$_2$ each represent a hydrocarbon group having from 1 to 6 carbon atoms or (ii)

wherein m is 2–6; and wherein n is 1 or 2.

2. The compound of claim 1 wherein X is —OH.
3. The compound of claim 2 wherein n is 1.
4. The compound of claim 3 wherein Y is structure (i) and wherein R$_1$ is —CH$_3$ and R$_2$ is —CH$_3$.

* * * * *